United States Patent [19]
Keim

[11] Patent Number: 5,771,888
[45] Date of Patent: Jun. 30, 1998

[54] TRACHEAL CANNULA FOR THE MECHANICAL RESPIRATION OF TRACHEOTOMISED PATIENTS

[75] Inventor: Michael Keim, Geroldshausen, Germany

[73] Assignee: Rusch AG, Kernen, Germany

[21] Appl. No.: 648,187

[22] PCT Filed: Nov. 8, 1994

[86] PCT No.: PCT/EP94/03647

§ 371 Date: Aug. 22, 1996

§ 102(e) Date: Aug. 22, 1996

[87] PCT Pub. No.: WO95/14499

PCT Pub. Date: Jun. 1, 1995

[30] Foreign Application Priority Data

Nov. 22, 1993 [DE] Germany ............ 43 39 706.9

[51] Int. Cl.[6] .................................. A61M 16/00
[52] U.S. Cl. .................. 128/207.15; 128/200.26; 128/207.14; 128/207.16
[58] Field of Search ............... 128/201.19, 200.26, 128/207.14, 207.15, 207.16; 604/284, 196; 623/9

[56] References Cited

U.S. PATENT DOCUMENTS

| | | | |
|---|---|---|---|
| 3,688,774 | 9/1972 | Ahiyama | 128/200.26 |
| 4,211,234 | 7/1980 | Fisher | 128/200.26 |
| 4,280,492 | 7/1981 | Latham | 128/207.15 |
| 4,304,228 | 12/1981 | Depel | 128/200.26 |
| 4,459,984 | 7/1984 | Liegner | 128/207.15 |
| 4,596,248 | 6/1986 | Lieberman | 128/207.16 |
| 4,852,565 | 8/1989 | Eisele | 128/207.14 |
| 5,056,515 | 10/1991 | Abel | 128/200.26 |
| 5,217,008 | 6/1993 | Lindholm | 128/200.26 |
| 5,458,139 | 10/1995 | Peast | 128/200.26 |

FOREIGN PATENT DOCUMENTS 3720482 12/1988 Germany ............ A61M 16/04

*Primary Examiner*—Vincent Millin
*Assistant Examiner*—V. Srivastava
*Attorney, Agent, or Firm*—Pandiscio & Pandiscio

[57] ABSTRACT

The invention relates to a tracheal cannula for the mechanical respiration of tracheotomised patients having a cuff which encloses and seals the proximal section which can be inserted concentrically in the trachea, a curved section arranged above the cuff and an inner cannula which can be inserted concentrically into the cannula from the distal end thereof, an exhalation opening being provided in the cannula above the cuff sealing the trachea and approximately in the extension of the longitudinal axis of the bent section insertable in the trachea, and, in its region lying beneath the exhalation opening, the inner cannula comprises an opening, which is at least partially covered by an elastic diaphragm acting as a valve, and at its proximal end the inner cannula comprises a region which is constricted in its cross section.

8 Claims, 2 Drawing Sheets

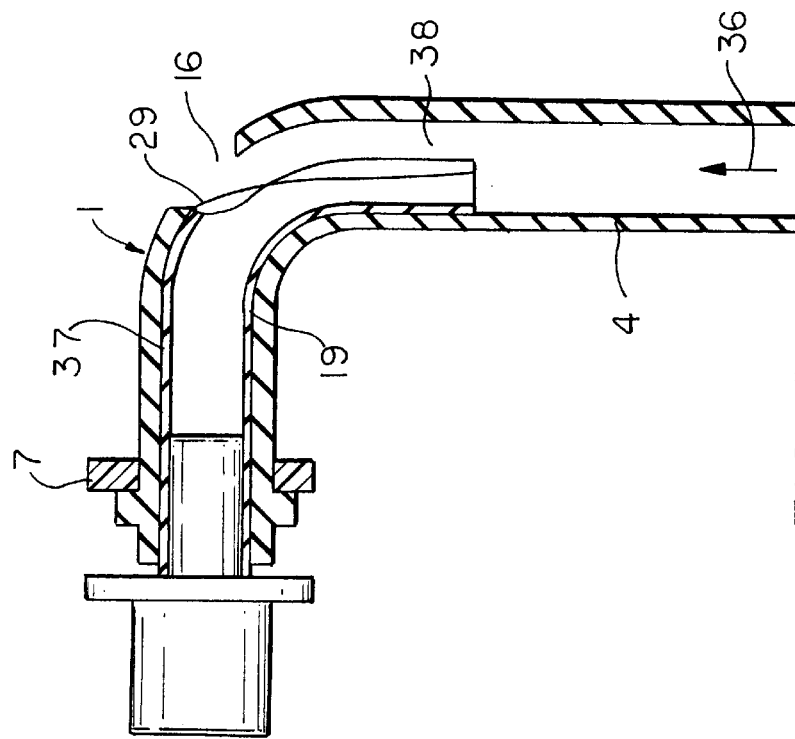
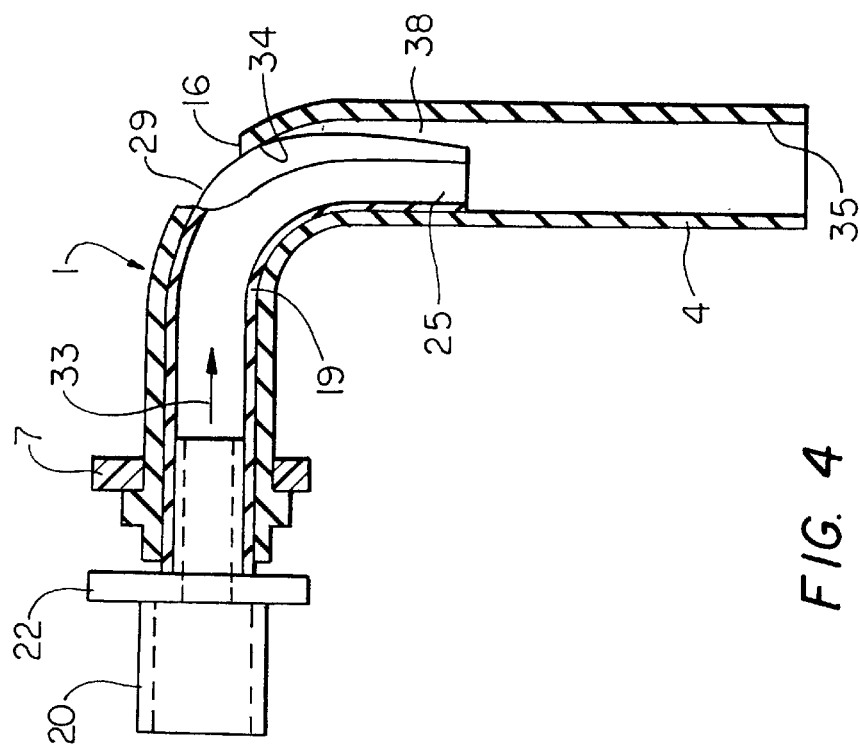

TRACHEAL CANNULA FOR THE MECHANICAL RESPIRATION OF TRACHEOTOMISED PATIENTS

BACKGROUND OF THE INVENTION

1. Field of the Invention

The invention relates to a tracheal cannula for the mechanical respiration of tracheotomised patients, the cannula having a cuff which encloses and seals the proximal section which can be inserted concentrically in the trachea, a curved section arranged above the cuff and an inner cannula which can be inserted concentrically into the cannula from the distal end thereof, an exhalation opening being provided in the cannula above the cuff sealing the trachea and approximately in the extension of the longitudinal axis of the bent section insertable in the trachea.

2. Description of the Prior Art

In order to prevent the danger of asphyxiation, it is necessary in certain cases to carry out a tracheotomy rather than intubation in order to provide mechanical respiration to a patient. After opening the trachea during this operation, a specially provided cannula having a length of approximately 10 cm and an internal diameter of approximately 1 cm is inserted. A so-called core, i.e. a second, inner cannula, is then inserted into this cannula from its distal end. This core is provided at its outer end with a connecting element, a so-called connector, for connection to a respirator.

In contrast to natural respiration, which by the activity of the diaphragm and the intercostal musculature produces a balance between atmospheric pressure and the intrapulmonary pressure, in mechanical respiration a specific air volume is forced through the tracheal cannula and the trachea into the lungs. This produces a pressure inside the lungs which is greater than atmospheric pressure. So that the pressure required to this end can be built up, it is necessary for the trachea to be sealed by a balloon (cuff) which lies in the trachea beneath the larynx. This sealing ensures that the air contained in the lungs can only escape through the trachea cannula as soon as a corresponding valve is opened in the respirator.

Thus, in mechanical respiration using a tracheal cannula, the airways located above the cuff sealing the trachea are completely bypassed. The exhalation volume can therefore no longer flow through the larynx. However, in order to produce sounds it is necessary for the exhalation flow to be forced through the closed glottis so that the vocal chords can be caused to vibrate. If there is no possibility of causing the air columns to vibrate with the aid of the vocal chords, then the patient cannot express any vowel sounds. These correspond to sounds of different pitch, strength and tone colour generated by the larynx. Whilst the patient can still produce noises with the aid of his lips, teeth, tongue and palate, and can therefore produce individual consonants, communication is entirely ruled out without vowel sounds.

U.S. Pat. No. 4,852,565 describes a tracheal cannula for mechanical respiration. It comprises an outer cannula which can be inserted in the trachea and a core, which can be introduced into the outer cannula and comprises an inner cannula and a connector for connection to a respirator. In order to carry out independent respiration, one or more openings are provided in the outer cannula above a cuff sealing the trachea and approximately in the extension of the longitudinal axis of the bent section which can be inserted into the trachea. However, in order to allow for respiration through the upper part of the trachea and in particular through the larynx, it is necessary to withdraw the inner cannula from the outer cannula, since the inner cannula seals the relevant openings in the outer cannula in its inserted state. The distal end of the outer cannula is then closed by means of a plug, so that the patient is forced to breathe independently and both the inhalation and the exhalation volumes have to flow through the larynx, so that the patient is able to speak as usual. However, because a complete separation from the respirator is necessary, application is limited to patients whose process of recovery is advanced to the point where they can breathe independently for at least some of the time. In the often extensively longer period during which mechanical respiration is essential for the patient, it is impossible to generate sounds using the known arrangement.

Furthermore, DE-PS 37 20 482 describes a tracheal cannula with a bent pipe which is introduced into the patient's trachea through a neck opening. Located within the bent pipe is a space which is enclosed by a diaphragm, is connected via a thin hose to external bellows and can be blown up like a balloon by said bellows, so that the exotracheal mouth of the cannula can be fully closed. However, like the tracheal cannula in U.S. Pat. No. 4,852,565, this tracheal cannula is only suitable for patients who can breathe unassisted, since mechanical respiration is completely inhibited once the exotracheal cannula mouth has been closed by means of the balloon-like valve. In contrast to the generic tracheal cannulas for mechanical respiration, the prior-known cannula in DE-PS 37 20 482 does not comprise a cuff so that the patient can breathe via the larynx when the cannula mouth is blocked. Consequently, there is also no exhalation opening at all in this cannula, since the corresponding volume of air flows not through, but around the cannula when the cannula opening is closed. As a result of the numerous structural differences, this prior-known arrangement is unsuitable for mechanically ventilated patients and therefore represents a more distant state of the art.

SUMMARY OF THE INVENTION

In view of the disadvantage of prior known arrangements, it is the object of the invention to construct a tracheal cannula in such a manner that sounds can be produced using the larynx in spite of mechanical respiration, so that the patient can also express vowel sounds and can therefore communicate.

To this end, in a tracheal cannula for the mechanical respiration of tracheotomised patients having a cuff which encloses and seals the proximal section which can be inserted concentrically in the trachea, a curved section arranged above the cuff and an inner cannula which can be inserted concentrically into the cannula from the distal end thereof, an exhalation opening being provided in the cannula above the cuff sealing the trachea and approximately in the extension of the longitudinal axis of the bent section insertable in the trachea, it is provided according to the invention that, in its region lying beneath the exhalation opening, the inner cannula comprises an opening, which is at least partially covered by an elastic diaphragm acting as a valve, and at its proximal end the inner cannula comprises a region which is constricted in its cross section. During the inhalation phase, a given volume of air is forced by the respirator through the inner cannula introduced from the distal end into the trachea, through the proximal region of the tracheal cannula and the trachea into the lungs. The air which is forced in has an excess pressure in relation to atmospheric pressure. This pressure differential is generated in particular between the internal space of the core and the region of the trachea located above the sealing cuff. Since an exhalation opening is arranged in the tracheal cannula precisely in this region of differential pressure, the latter acts directly upon the underlying inner cannula. The inner cannula is formed in the region in question as an elastic diaphragm, which expands outwards or contracts inwards depending on the direction of the differential pressure. When air is forced at excess pressure into the lungs by the respirator, the diaphragm disposed in the inner cannula expands outwards in the region of the exhalation opening of the tracheal cannula and comes to rest against the inner surface of the cannula along the circumferential edge of the exhalation opening. As a result, the exhalation opening is sealed and the forced-in air is prevented from escaping directly through the upper airways instead of flowing into the lungs.

However, as soon as the outflow valve is opened in the respirator, the exhalation phase begins. The volume of air which is located in the lungs at excess pressure then firstly flows through the lower region of the trachea, the tracheal cannula and the inner space of the inner cannula and the connector to the respirator, whence it escapes through the outflow valve to the environment. As a result of the constricted cross section of the region at the proximal end of the inner cannula, the flow velocity of the outflowing air is restricted, so that the exhalation volume flows out at a reduced velocity. Consequently, the excess pressure in the lungs is maintained, whilst the air can flow almost unimpeded to the respirator above the constricted cross sectional region within the inner cannula. The air pressure in this upper region is therefore reduced approximately to atmospheric pressure, so that the elastic diaphragm contracts into its original position once the expanding differential pressure subsides. However, in this state the diaphragm no longer rests against the inside of the tracheal cannula in the region of the circumferential edges of the exhalation opening. Consequently, a second flow path is opened for a proportion of the exhalation volume, namely outwards through the trachea, the proximal region of the tracheal cannula, the intermediate space between the constricted region of the inner cannula and the inner wall of the tracheal cannula, its exhalation opening and the upper region of the airways, in particular the larynx. The proportion of the exhalation volume flowing through the larynx is able, by way of the vocal chords, to bring about a vibration of the air columns, so that the patient can produce sounds as usual and transform these into vowels. During the exhalation phase, it is therefore possible for the patient to communicate with his environment as usual by way of speech. In addition, the upper airways are also heated, moistened and cleaned. Finally, the proportion of the exhalation volume flowing through the upper airways also enables the patient to smell, since the exhalation volume can flow over the olfactory plate.

An advantageous further development of the invention consists in that the opening in the inner cannula covered by an elastic diaphragm extends in the manner of a slot as far as the proximal end face of the inner cannula. The opening thus forms a slot which opens into the proximal end face of the inner cannula. This offers the advantage that the cross section of the proximal end of the inner cannula can vary according to the direction of flow of the air located within the inner cannula. More particularly, it is possible in this manner for the diaphragm to expand outwards in this region of the inner cannula during the inhalation phase under the pressure of flow of the air flowing into the lungs, so that the air flow is less impeded.

On the other hand, in the absence of a flow the diaphragm contracts in its proximal region and adopts a position in which it directly connects the slot edges with one another without any noticeable curvature. In this case, the diaphragm approximately forms a secant in cross section, which divides the circular cross section of the inner cannula between the two slot edges into a section lying within the inner cannula and an intermediate space remaining between the diaphragm and the inner wall of the cannula. This results at the start of the exhalation phase in a constriction of the flow cross section, at which almost the entire excess pressure in the lungs generating the exhalation flow drops.

As a result of the ensuing fall in pressure in the region of the cannula bend, the diaphragm also contracts to its own cross section in its upper region located directly beneath the exhalation opening and thereby releases the exhalation opening. The release of the diaphragm from the exhalation opening is additionally supported as a result of the fact that the same excess pressure exists, at least initially, within the intermediate space remaining between the intermediate wall of the cannula and the diaphragm as inside the lungs, whilst scarcely no more excess pressure exists beneath the diaphragm, i.e. within the core, after the start of the exhalation flow. In this phase, the excess pressure therefore acts upon the diaphragm in precisely the opposite direction and thus pushes the diaphragm further away from the exhalation opening. The exhalation opening is thereby fully released and most of the exhalation volume takes the route via the upper airways.

It has proved expedient for the slot-like opening in the inner cannula which is covered by an elastic diaphragm to adopt a cross section at its proximal end which corresponds to approximately half the curvature circumference of the cross section of the core. With this type of design, the action of the elastic diaphragm is maximal. On the one hand, the diaphragm can already expand when there is a low flow velocity during the inhalation phase, thereby releasing almost the entire cross section of the core; on the other hand at the start of the exhalation phase it constricts the cross section in its relaxed state to approximately half the cross section of the core, which is entirely adequate for a pressure reduction in the upper diaphragm region.

Once the exhalation flow has begun via the upper airways, the diaphragm expands in its lower region as a function of the pressure conditions within the distal region of the inner cannula and the upper airways of the patient, the flow path with the higher pressure being expanded in each case. This offers the advantage that during speech, when the exhalation volume needs to be forced through the vocal chords and thereby experiences increased air resistance, the diaphragm is forced inwards by the resulting excess pressure, so that a relatively large proportion of the air flow finds its way via the larynx and in so doing supports the production of sound. As a result of the diaphragm, a large volume of air is conveyed through the larynx precisely at that moment when the patient wants to speak.

Furthermore, it is advantageous for the elastic diaphragm, in its extensively relaxed state, to comprise a reduced circumference in its proximal region in relation to the exhalation opening as compared with the curvature circumference of the cross section of the inner cannula. This prevents the diaphragm from resting against the inside of the tracheal cannula on the one hand and the inside of the inner cannula on the other and prevents one of the two flow paths from being completely closed. This ensures that exhalation can also take place via the respirator when the upper airways are completely closed. This fully rules out a complication which could arise as a result of the diaphragm resting against the inside of the inner cannula at the start of the exhalation phase, which would render exhalation impossible if the upper airways were blocked—a fact which needs to be taken into account in order to prevent asphyxiation. With the dimensioning provided according to the invention, the diaphragm never fully moves with its proximal end as far as the inside of the cannula or the inner cannula. Both flow paths are therefore always open during the exhalation phase, which even increases the patient's safety as compared with conventional tracheal cannulas, since at least the flow path via the upper airways is available in the event of failure of the outflow valve in the respirator.

In addition, it is provided in accordance with the invention that the elastic diaphragm has a circumference in its relaxed state in the region lying beneath the exhalation opening corresponding approximately to the curvature circumference of the cross section of the inner cannula. As a result of this dimensioning, the exhalation opening is already completely closed at the start of the inhalation phase, so that the excess pressure in the cannula, trachea and lungs can be built up slowly and uniformly by means of the respirator, thereby reproducing the natural respiration process. On the other hand, when the exhalation opening is released, the diaphragm can move easily in this region as a function of the pressure conditions from the convex curvature resting against the inside of the cannula into a concave curvature reaching far into the inner space of the core, so that—particularly during speech—almost the entire air flow can reach the glottis without any significant drop in pressure, so that it is even possible to produce loud sounds. This is because the strength of the sounds depends upon the amplitude of the vibrations which are generated, which is in turn dependent upon the pressure with which the exhalation air is forced through the glottis.

It falls within the scope of the invention for the inner cannula to comprise a radial abutment element for limiting the insertion movement into the cannula, which in the case of tracheal cannulas having a connector connected to the inner cannula and acting as a connecting element for a respirator is more particularly preferably moulded onto the connector. By limiting the insertion movement of the inner cannula, it is easily possible to adjust a defined position of the inner cannula, so that an alignment of the exhalation opening and the slot-like opening is ensured.

Finally, it falls within the teaching of the invention that an annular retaining web is displaceably and fixably arranged on the distal section of the cannula lying above the bend. After insertion into the trachea, the tracheal cannula according to the invention is fixed by means of a cannula strap looped around the neck of the patient. This strap is suspended in diametrally opposing openings in a retaining plate, which encloses the distal section of the cannula. As a result of the elasticity of the retaining strap looped around the patient's neck, the retaining web is pressed securely against the patient's neck. In conventional tracheal cannulas, where the retaining web is integrally formed with the cannula, this situation does not have a negative effect, since the cannula itself is elastic and can be inserted to differing degrees into the trachea according to the neck circumference of the patient. However, in the tracheal cannula according to the invention, it is necessary to adapt the position of the retaining plate to the neck circumference of the patient, so that the exhalation opening arranged in the curved region lies exactly beneath the upper region of the trachea. Only in this way is a flow path via the upper airways, which allows for articulation, possible. In order to realise a displaceable and fixable retaining web, it is possible, for example, to select an internal diameter of the opening in the retaining web accommodating the distal cannula end which is slightly smaller than the outer circumference of the cannula, so that the retaining web is pushed onto the cannula with elastic expansion. The resulting elastic contact force results in a high frictional force between the cannula and retaining web, so that the latter cannot be dislodged on the cannula under normal operating conditions. It is nevertheless possible—for example during an operation—to adapt the retaining web to the neck circumference of the patient. It is, for example, also conceivable to provide markings on the cannula, on which the retaining web can be positioned according to the neck circumference of the patient.

Further details, features and advantages on the basis of the invention are described in the following description of a preferred embodiment of the invention with the aid of the drawings, in which:

BRIEF DESCRIPTION OF THE DRAWINGS

FIG. 4 is a longitudinal section through the tracheal cannula according to FIG. 1 fitted with the core according to FIG. 3 during the inhalation phase; and FIG. 5 is longitudinal sectional view similar to FIG. 4, showing the cannular in the exhalation phase.

DESCRIPTION OF THE PREFERRED EMBODIMENT

Figure 3:
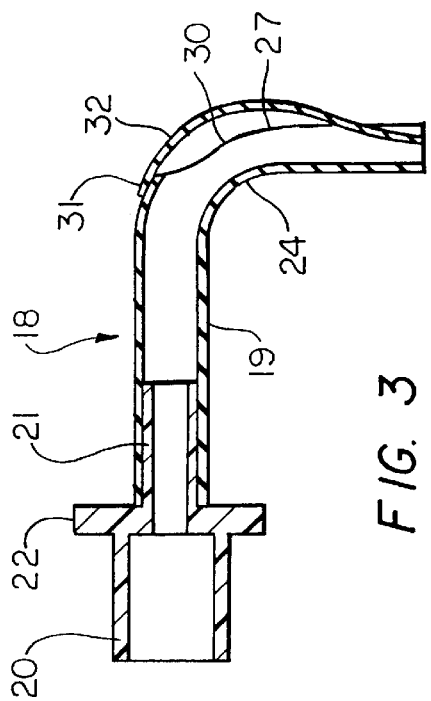
FIG. 3 is a longitudinal section through the core according to FIG. 2.

The structure of the tracheal cannula 1 according to the invention is essentially similar to the tracheal cannula known from the state of the art. The cannula 1 is made of elastic, physiologically compatible material. It has the form of a bent pipe 2 with a circular cross section. This pipe 2 has an internal diameter of approximately 1 cm and an overall length of approximately 10 cm. An approximately right-angled bend 3 of the cannula pipe 2 is located in the latter's central region and divides the cannula pipe 2 into a lower section 4 which can be inserted into the trachea of a patient, and an upper section 5 penetrating the windpipe incision.

In order to fix a distal end 6 of the tracheal cannula 1 to the neck of the patient, an annular retaining web 7 is used, which in its lateral regions comprises two brackets diametrally opposed to one another, each comprising an opening in which a securing strap can be suspended.

So that the air forced in by the mechanical respiration cannot pass into the upper region of the trachea through an intermediate space which may remain between the outside of the section 4 of the cannula 1 inserted into the trachea and the inner surface of the trachea, and from there escape via the upper airways, a balloon 9 filled with elastic foam material 8 is arranged so as to enclose the lower section 4 of the cannula pipe 2. This arrangement referred to as the cuff 10 provides air-tight sealing of an intermediate space between the cannula pipe 2 and the trachea.

Figure 1:
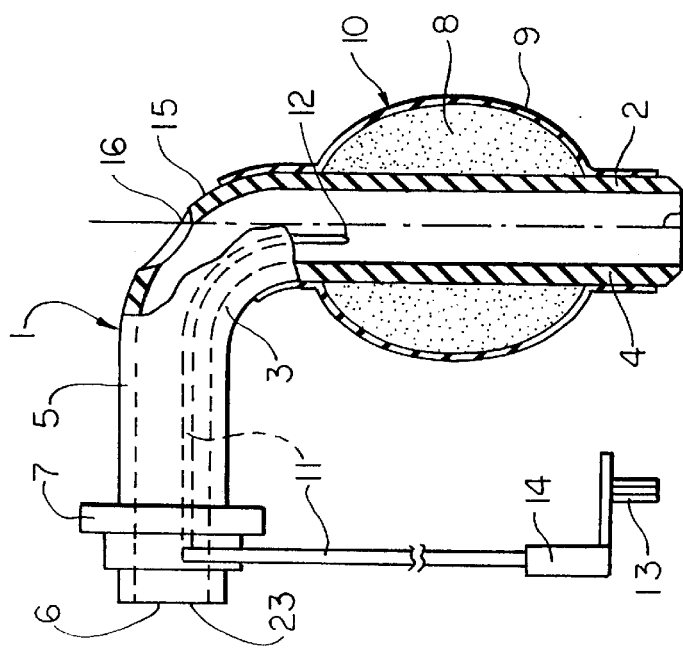
FIG. 1 is a side elevational view of a tracheal cannula according to the invention, partially shown in section.

So that the cuff 10 can be pushed through the windpipe incision during insertion, a vacuum can be generated in the tube-like region between the cannula tube lower section 4 and the balloon casing 9 filled with elastic foam material, so that atmospheric air pressure presses against the cannula tube lower section 4 against the elastic force of the foam material 8 of the balloon casing 9. In order to generate a vacuum of this type, a hose 11 is provided, which extends within the upper section 5 of the cannula 1 and opens at its proximal end 12 within the cuff 10 into the cavity between the cannula tube lower section 4 and the balloon casing 9 filled with foam material 8 via an opening which lies outside the plane of the drawing of FIG. 1 and penetrates the cannula tube lower section 4. At the distal end 6 of the cannula 1, the hose 11 extends outwards and ends in a mouthpiece 14 which is closable by a plug 13. A vacuum generated within the cuff 10 prior to the insertion of the tracheal cannula 1 can be maintained for any desired length of time by closing the mouthpiece 14 by means of the plug 13. When the plug 13 is removed from the mouthpiece 14 after the insertion of the cannula 1, air can enter the cuff 10 via the hose 11, so that the cuff 10 expands under the action of the enclosed, elastic foam material 8 and thereby seals the trachea in an air-tight manner.

In order to still allow the patient articulation, an approximately circular or oval exhalation opening 16 is provided in the radially outer region 15 of the pipe 2 in relation to the bend 3. As a result of the bend 3 in the cannula 1, the exhalation opening 16 lies approximately in the region of the longitudinal axis 17 of the lower section 4 of the cannula 1 fitted in the trachea. The exhalation opening 16 therefore lies precisely within the upper region of the trachea which is aligned with the section into which the cannula pipe lower section 4 is inserted. The exhalation opening 16 therefore acts as a connection to the upper airways.

So that the exhalation opening 16 can be placed exactly beneath the upper tracheal region during the insertion of the tracheal cannula 1, the retaining web 7 is arranged so as to be linearly displaceable along the distal section of the tracheal cannula 1. As a result of its elasticity, it is able to generate a large frictional force at any desired location and can therefore lock in an almost non-displaceable manner. In this manner, it is possible to take the different neck widths of tracheotomised patients into account.

So that the exhalation opening 16 can be opened and closed in differentiated fashion according to the respiration phase, a specially shaped core 18 is provided. The core 18 comprises a section 19, also made of elastic plastics material, which can be pushed as a second, inner cannula into the distal end 6 and upper section, 5 of the cannula 1, and a connector 20, which acts as a connecting element for a respirator. The slightly elastic inner core section 19 is pushed with radial expansion onto a corresponding extension 21 of the connector 20, so that a secure connection is formed between the inner core section 19 and the connector 20 as a result of the high frictional force.

The inner core section 19 is pushed into the distal end and upper section 5 of the tracheal cannula 1 until a radial abutment element 22 of the connector 20 rests against the distal end face 23 of the tracheal cannula 1. In this respect, a bend 24 in the inner core section 19 matches the bend 3 in the tracheal cannula 1.

Figure 2:
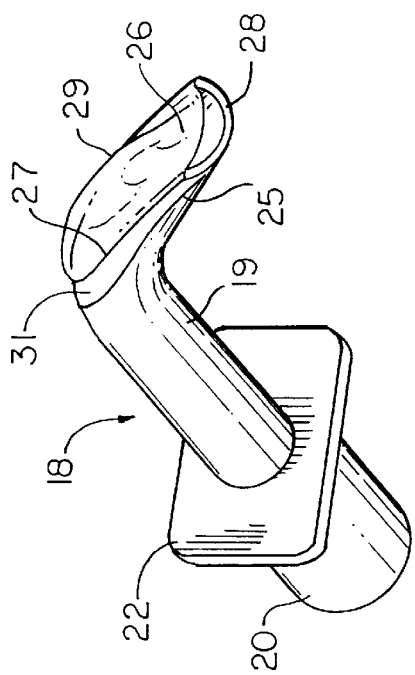
FIG. 2 is a perspective view of a core according to the invention which is to be fitted in the tracheal cannula according to FIG. 1.

As best seen in FIG. 2, the inner core section 19 comprises a longitudinal slot 26 at its proximal end 25, which slot extends on the radially outer side 27 in relation to the bend 24 from the proximal end face 28 almost over the entire region of the bend 24. The circumference of the slot 26 forms an approximate U-shape. The maximum slot width of the slot 26 is approximately equal to the diameter of the inner core section 19.

This slot-like opening 26 in the outer surface of the inner core section 19, which although slightly elastic is relatively rigid as a whole, is covered by a wafer-thin, highly elastic diaphragm 29, which is bonded in an air-tight manner to the inner core section 19 along a region 31 overlapping the circumferential edge 30 of the opening 26. The diaphragm 29 curves outwards in its relaxed state in the region 32 of the bend 24 and therefore lies approximately at the location formerly occupied by the region of the inner core section 19 substituted by the opening 26. In the region of the proximal end 25 of the inner core section 19, this curvature firstly decreases gradually until finally, just above the end face 28, the diaphragm 29 extends in a slightly stretched form between the two opposing circumferential edges 30 of the slot-like opening 26. However, at the height of the end face 28, the curvature increases again. As a result of the internal tensions within the diaphragm 29, the latter bulges outwards in the upper region 32, whilst it curves slightly inwards in the region of the end face 28.

FIG. 4 shows the two cannulas 1, 19 (the latter comprising the core section) inserted one within the other during the inhalation phase of a tracheotomised, mechanically ventilated patient. As a result of the excess pressure generated by the respirator, not shown, relative to the emptied lungs, a flow 33 is generated in the direction of the proximal end of the cannulas 1, 19. The expansion of the thorax required for filling the lungs is impeded on the one hand by the external air pressure and on the other hand by the weight of the thorax. Consequently, the excess pressure generated by the respirator spreads through the connector 20, the inner cannula 19 and the proximal lower section 4 of the tracheal cannula 1 and the trachea into the lungs.

As a result of the proximal end region 25 of the inner cannula 19 which is constricted by the diaphragm 29, the air accumulates at this point and as a consequence of the resulting excess pressure relative to the proximal section 4 of the tracheal cannula 1 an expanding force acts upon the diaphragm 29 in a radially outward direction in relation to the bend 24. Consequently, the diaphragm 29 comes to rest in an air-tight manner against the inside 35 of the tracheal cannula 1 along the inner circumferential edge 34 of the exhalation opening 16. The exhalation opening 16 is thereby closed and prevents the air volume forced into the airways by the respirator during the inhalation phase from escaping through the exhalation opening 16.

The exhalation opening 16 remains closed so long as the pressure in the connected airways is greater than atmospheric pressure. However, when an outflow valve is opened in the respirator, a flow 36 can be generated in the opposite direction as shown in FIG. 5. Whilst the excess pressure is quickly reduced within the distal section 37 of the inner cannula 19, the connector and the respirator, given that the air volume contained therein can flow outward without resistance, the excess pressure in the lungs, trachea and proximal section 4 of the tracheal cannula 1 decreases relatively slowly, since the flow 36 in this region is greatly decelerated by the proximal end constriction 25 in the flow cross section. This means that the pressure existing in the inner space 38 between the diaphragm 29 and the inside 35 of the cannula pipe lower section 4 is greater than the pressure within the inner cannula 19 which is reduced to a greater degree by the outflow of air. As a result of this differential pressure, the diaphragm contracts and is finally even forced in the opposite direction, i.e. curves in a concave fashion. In so doing, the diaphragm moves away from the circumferential edges 34 of the exhalation opening 16, so that an air duct is opened via the upper airways, more particularly the larynx. It is therefore possible for the patient to generate sounds with the aid of the exhalation volume forced through the glottis, to form these sounds into vowels and with the addition of the required consonants to communicate as usual.

When the glottis constricts during speech, the flow cross section in the larynx is reduced, so that the excess pressure contained in the lungs can spread, almost unchanged, as far as the glottis. As a result of this excess pressure, which also exists more particularly in the region of inner space 38 between the diaphragm 29 and the inner wall 35 of the cannula pipe lower section 4, the diaphragm 29 is completely folded back and finally even stretched in the opposite direction, so that the flow path remaining within the inner cannula 19 is also greatly constricted and only a small quantity of air escapes through the respirator. Consequently, almost the entire lung pressure is available to the patient during speech. Furthermore, this pressure is maintained for a particularly long period of time, since only a small proportion flows through the respirator. It is therefore also possible for the patient to speak longer sentences during an exhalation phase.

I claim:

1. A tracheal cannula assembly for mechanical respiration of tracheotomised patients said cannula assembly comprising an outer cannula (1) having a cuff (10) which is adapted to enclose and seal a proximal section (4) of said outer cannula (1) in a trachea, which section (4) is insertable in a trachea, said outer cannula having a curved section (3) arranged adjacent the cuff (10), and an inner cannula (19) disposed substantially concentrically in said outer cannula (1), an exhalation opening (16) being provided in said outer cannula (1) proximate said cuff (10), and disposed proximate a hypothetical extension of a longitudinal axis (17) of the proximal section (4), characterised in that in a portion of said inner cannula adjacent the exhalation opening (16), the inner cannula (19) is provided with an elongated opening (26) in a side wall of said inner cannula (19) and extending from a proximal end (25) of said inner cannula (19), which opening (16) is at least in part covered by an elastic diaphragm (29) operable as a valve, and at said proximal end (25) thereof is provided with an end opening constricted in cross section.

2. A tracheal cannula assembly according to claim 1, characterised in that the elongated opening (26) in the inner cannula (19) comprises a slot (26) which extends to a proximal end face (28) of the inner cannula (19).

3. A tracheal cannula assembly according to claim 2, characterised in that, at said proximal end (25), the slot (26) in the inner cannula (19) is of a cross section which is substantially half the cross section of a curvature circumference of said inner cannula proximal end (25).

4. A tracheal cannula assembly according to claim 3, characterised in that said elastic diaphragm (29) has a circumference which is smaller, in a relaxed state, than the curvature circumference of said inner cannula proximal end 25.

5. A tracheal cannula assembly according to claim 1, characterised in that in a region (32) of said inner cannula (1) adjacent said exhalation opening (16) of said outer cannula the elastic diaphragm (29), in a relaxed state, has a circumference substantially corresponding to the curvature circumference of the cross section of the inner cannula (19).

6. A tracheal cannula assembly according to claim 1, characterised in that the inner cannula (19) is provided with a radial abutment element (22) for limiting insertion movement of said inner cannula 19 into said outer cannula (1).

7. A tracheal cannula assembly according to claim 6 and further comprising a connector (20) connected to the inner cannula (19) and which acts as a connection element for a respirator, characterised in that the radial abutment element (22) is moulded onto the connector (20).

8. A tracheal cannula assembly according to claim 1, characterised in that an annular retaining web (7) is displaceably and fixably arranged on a distal section (5) of the outer cannula (1) and spaced from the bend (3).

* * * * *